(12) United States Patent
Jung et al.

(10) Patent No.: US 8,724,106 B2
(45) Date of Patent: May 13, 2014

(54) METHOD OF QUANTITATIVELY ANALYZING URANIUM IN AQUEOUS SOLUTIONS

(75) Inventors: Euo Chang Jung, Daejeon (KR); Hye-Ryun Cho, Daejeon (KR)

(73) Assignees: Korea Atomic Energy Research Institute (KR); Korea Hydro & Nuclear Power Co., Ltd. (KR)

( * ) Notice: Subject to any disclaimer, the term of this patent is extended or adjusted under 35 U.S.C. 154(b) by 118 days.

(21) Appl. No.: 13/337,796

(22) Filed: Dec. 27, 2011

(65) Prior Publication Data

US 2012/0176603 A1    Jul. 12, 2012

(30) Foreign Application Priority Data

Jan. 6, 2011   (KR) ................. 10-2011-0001302

(51) Int. Cl.
*G01J 3/44*   (2006.01)
(52) U.S. Cl.
USPC ........................................................ 356/301
(58) Field of Classification Search
USPC ........ 356/301; 250/255, 459.1; 436/525, 180; 205/46
See application file for complete search history.

(56) References Cited

U.S. PATENT DOCUMENTS

| | | | | |
|---|---|---|---|---|
| 4,641,032 | A | * | 2/1987 | Mauchien et al. ......... 250/459.1 |
| 5,796,476 | A | * | 8/1998 | Wang et al. .................. 356/301 |
| 2003/0109061 | A1* | | 6/2003 | Eaton et al. .................. 436/180 |
| 2013/0206599 | A1* | | 8/2013 | Celier ............................. 205/46 |

FOREIGN PATENT DOCUMENTS

| | | |
|---|---|---|
| EP | 1548464 A1 | 6/2005 |
| JP | 61066158 A | 4/1986 |
| JP | 2009103479 | 5/2009 |
| JP | 2009103479 A * | 5/2009 |

OTHER PUBLICATIONS

English Abstract of JP Publication No. 2009-103479, published May 14, 2009, 1 page.
Jung, et al., "Study on the Chemical Speciation of Hydrolysis Compounds of U(VI) by Using Time-Resolved Laser-Induced Fluorescence Spectroscopy," J. of the Korean Radioactive Waste Society, vol. 7(3), p. 133-141, Sep. 2009, 9 pages.

* cited by examiner

*Primary Examiner* — Tarifur Chowdhury
*Assistant Examiner* — Jamil Ahmed
(74) *Attorney, Agent, or Firm* — Fredrikson & Byron, P.A.

(57) ABSTRACT

Disclosed herein is a method of quantitatively analyzing uranium in an aqueous solution, the method comprising measuring Raman scattering intensity of water and luminescence intensity of uranium standard solutions having various concentrations (Operation 1); calculating a ratio of the uranium luminescence intensity to the Raman scattering intensity of water for each uranium concentration and plotting a calibration curve therethrough (Operation 2); and measuring Raman scattering intensity of water and uranium luminescence intensity of an unknown sample, calculating a ratio of the measured intensities and determining a uranium concentration thereof by using the calibration curve (Operation 3).
When the quantitative analysis method of uranium in an aqueous solution according to the present invention is used, inconvenience of a typical analysis method, in which repetitive measurements of calibration curves are required according to various measurement conditions, may be removed.

4 Claims, 6 Drawing Sheets

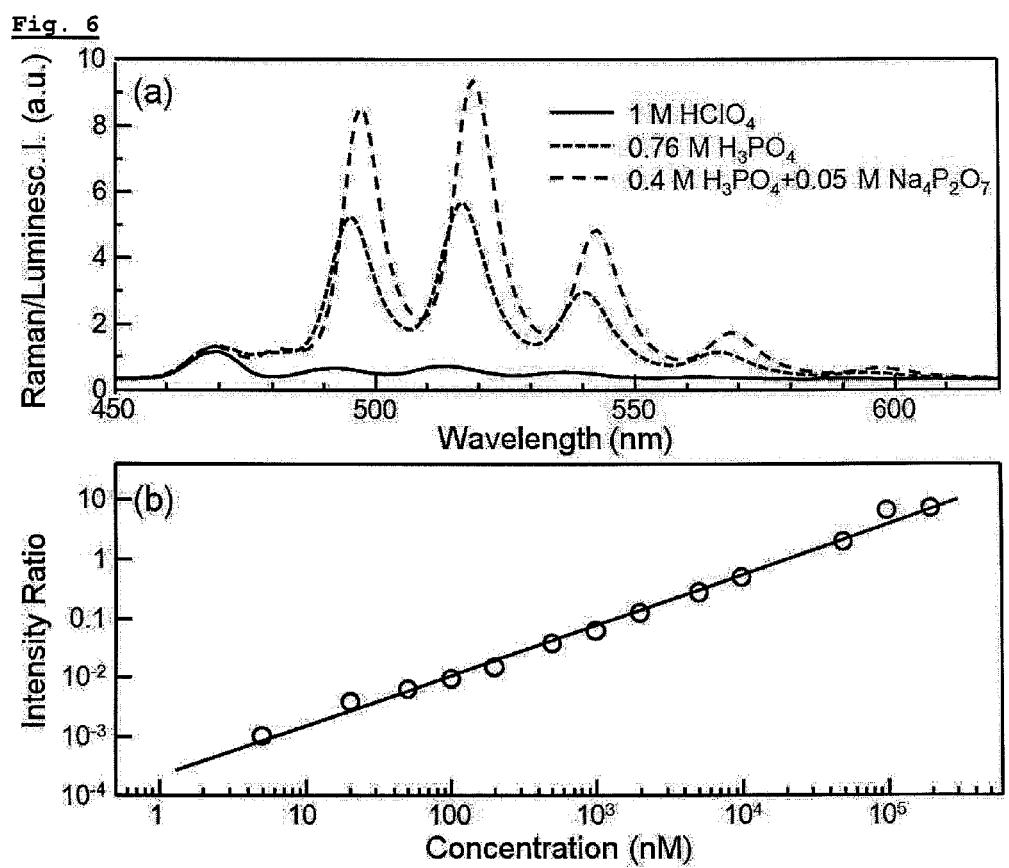

METHOD OF QUANTITATIVELY ANALYZING URANIUM IN AQUEOUS SOLUTIONS

CROSS-REFERENCES TO RELATED APPLICATION

This patent application claims the benefit of priority from Korean Patent Application No. 10-2011-0001302, filed on Jan. 6, 2011, the contents of which are incorporated herein by reference.

BACKGROUND OF THE INVENTION

1. Field of the Invention

The present disclosure relates to a method of quantitatively analyzing uranium in an aqueous solution by using a ratio between Raman scattering intensity of water and luminescence intensity of uranium.

2. Description of the Related Art

Since ground water plays an important role in transport and redistribution of elements constituting the Earth's crust, there are many cases in which techniques for measuring environmental radioactive isotopes in ground water can be a useful means of geochemical and mineral exploration research. Most of radioactive isotopes in ground water are generated from actinide elements such as uranium and thorium that exist in nature. Uranium among natural radioactive elements particularly causes harm to health by being accumulated in bones and kidneys when ingested. With respect to uranium, chemical risk is greater than radioactivity. According to the evaluation by international commission on radiological protection (ICRP), it has been known that about 5% of ingested uranium is generally absorbed into blood stream through stomach. With respect to the foregoing risk of uranium, the U.S. environmental protection agency (EPA) was established maximum contamination levels (MCL) for environmental radioactive isotopes in public drinking water as the national interim primary drink water regulation (NIPDRW) in 1976.

Since uranium used as nuclear fuel exists in a trace amount in sea water, earth's surface, and environmental samples, an analysis method having a low detection limit has been required in order to quantitatively analyze uranium. In analysis methods of uranium reported to date, a titration method, absorption spectrometry using a spectrophotometer, fluorescence spectrometry using a fluorophotometer or a pulse laser light source, and chromatography have been widely used. However, the foregoing methods have limitations of a pretreatment process of a sample, matrix effects, prolonged analysis time, and requirements of expensive equipments and high costs.

U.S. Pat. No. 4,641,032 relates to a method of quantitatively analyzing a trace amount of uranium in a solution by using fluorometry. Luminescence of uranium molecules in the solution is generated by the incident of a pulsed laser beam. At this time, uranium luminescence signals decreased as an exponential function of time are recorded and initial intensities ($I_0$) of uranium luminescence excluding laser pulse signals with respect to a uranium standard solution and an unknown uranium sample are measured. The method then quantitatively analyzes uranium by comparing the initial luminescence intensities thereof.

Korean Patent Application Laid-Open Publication No. 1994-0011945 relates to a nitrogen laser-induced uranium fluorescence analysis apparatus using optical fibers, in which a uranium concentration is quantitatively analyzed by measuring uranium luminescence emitted when a uranium aqueous solution is irradiated with a pulsed nitrogen laser beam. The foregoing analysis apparatus is characterized by that a nitrogen laser beam is incident on a sample-charged optrode by using optical fibers for laser beam transmission and generated luminescence signals are collected with optical fibers for luminescence transmission so as to be incident to an oscilloscope as a detector.

All the typical methods for quantitative analyzing uranium must obtain a calibration curve for measuring the concentration thereof by preparing standard samples having different concentrations in order to quantitatively analyze uranium in an unknown sample. Since the calibration curve may be different according to the intensity of a light source and the sensitivity of a detector, works for obtaining the calibration curve may be inconvenient because the works must be repeated whenever an unknown sample is measured.

Therefore, the present inventors developed a method of quantitatively analyzing uranium in an aqueous solution by using a ratio between Raman scattering intensity of water and uranium luminescence intensity, and confirmed that the foregoing method is effective in uranium analysis because the detection limit thereof is as low as that of a commercial analysis apparatus, thereby leading to completion of the present invention.

SUMMARY OF THE INVENTION

One object of the present invention is to provide a method of quantitatively analyzing uranium in an aqueous solution by using a ratio between Raman scattering intensity of water and uranium luminescence intensity.

In order to achieve the objects, the present invention provides a method of quantitatively analyzing uranium in an aqueous solution including: measuring Raman scattering intensity of water and luminescence intensity of uranium standard solutions having various concentrations (Operation 1); calculating a ratio of the uranium luminescence intensity to the Raman scattering intensity of water for each uranium standard solution and plotting a calibration curve therethrough (Operation 2); and measuring Raman scattering intensity of water and uranium luminescence intensity of an unknown sample, calculating a ratio of the measured intensity and determining a concentration thereof by using the calibration curve (Operation 3).

BRIEF DESCRIPTION OF THE DRAWINGS

The above and other objects, features and other advantages of the present invention will be more clearly understood from the following detailed description taken in conjunction with the accompanying drawings, in which:

FIG. 6(a) is luminescence spectra of uranium in three different solutions which are 1 M HClO$_4$, 0.76 M H$_3$PO$_4$ and a mixed solution of 0.4 M H$_3$PO$_4$ and 0.05 M Na$_4$P$_2$O$_7$ measured by using a semiconductor laser; and FIG. 6(b) is a calibration curve illustrating a ratio of luminescence intensity of uranium to Raman scattering intensity of water according to the concentration of uranium in a mixed solution of 0.4 M H$_3$PO$_4$ and 0.05 M Na$_4$P$_2$O$_7$ measured by using a semiconductor laser when detector sensitivity is changed.

DESCRIPTION OF THE PREFERRED EMBODIMENTS

Figure 1:
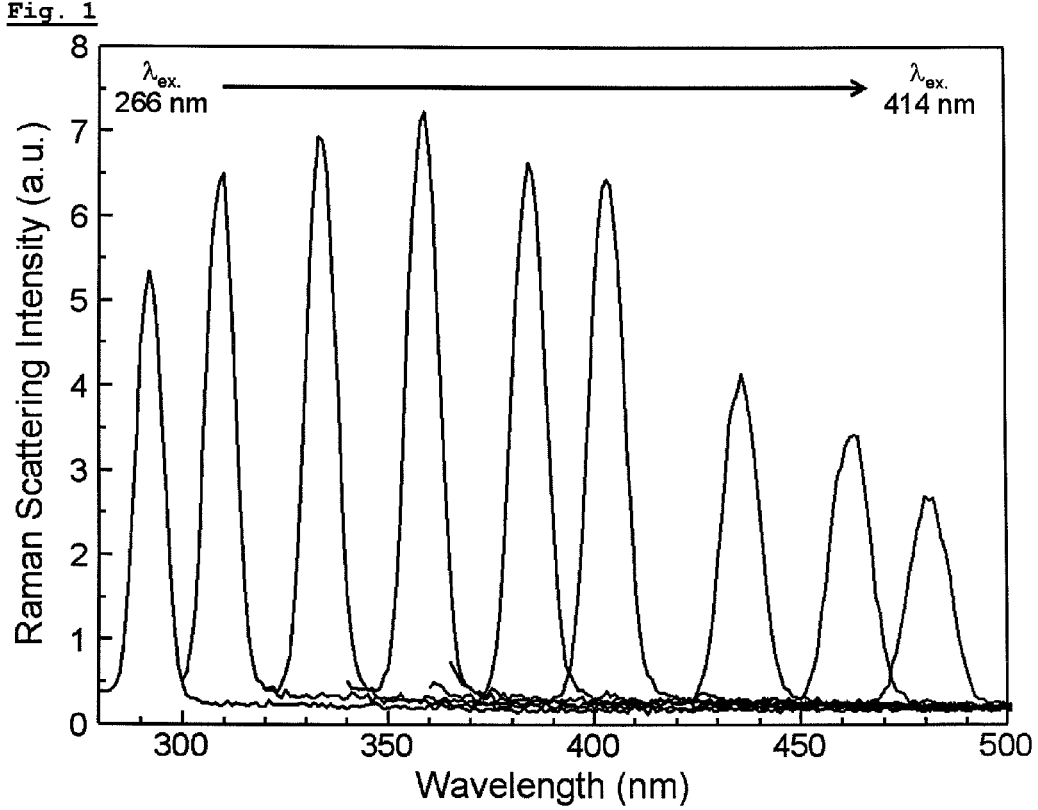
FIG. 1 is a spectrum illustrating changes in a Raman scattering peak position of water when a wavelength incident on a sample is changed.

Hereinafter, the present invention will be described in detail.

The present invention provides a method of quantitatively analyzing uranium in an aqueous solution including:

measuring Raman scattering intensity of water and luminescence intensity of uranium standard solutions having various concentrations (Operation 1);

calculating a ratio of the uranium luminescence intensity to the Raman scattering intensity of water for each uranium standard solution and plotting a calibration curve for measuring the concentration of uranium therethrough (Operation 2); and measuring Raman scattering intensity of water and uranium luminescence intensity of an unknown sample, calculating a ratio of the measured intensities and determining a concentration thereof by using the calibration curve (Operation 3).

When the quantitative analysis method of uranium in an aqueous solution according to the present invention is used, inconvenience of a typical analysis method, in which repetitive measurements of calibration curves are required according to various measurement conditions, may be removed. Also, when a laser is used as a light source, the quantitative analysis method of the present invention may be used for the analysis of a trace amount of uranium because the detection limit thereof is as low as those of inductively coupled plasma atomic emission spectrometry (ICP-AES), inductively coupled plasma mass spectrometry (ICP-MS), and a commercial analysis instrument such as a kinetic phosphorescence analyzer (KPA). Further, when a GaN semiconductor laser having a violet wavelength range is used, miniaturization of an analysis apparatus may be possible.

Hereinafter, the present invention will be described in detail operation by operation.

Operation 1 of the present invention is measuring Raman scattering intensity of water and luminescence intensity of uranium standard solutions having various concentrations. At least three or more of uranium standard solutions are prepared and Raman scattering intensities of water and uranium luminescence intensities are measured therefrom. A light source used at this time may be an ultraviolet ray or a blue laser beam. The reason for this is that the uranium luminescence intensity increases as a wavelength having strong intensity in an excitation spectrum with respect to uranium samples is used. Also, when a small semiconductor laser having a violet wavelength range is used as a light source, miniaturization may be possible in comparison to a commercial analysis apparatus.

Operation 2 of the present invention is calculating a ratio of the uranium luminescence intensity to the Raman scattering intensity of water for each uranium standard solution and plotting a calibration curve therethrough. The calibration curve is plotted with the uranium concentration of the prepared standard solution as x-axis and a value obtained by dividing the luminescence intensity measured for each concentration by the measured Raman scattering intensity as y-axis. Since the calibration curve plotted in the foregoing operation is unchanged according to measurement conditions such as the intensity of a light source and the sensitivity of a detector, the calibration curve once plotted may be used continuously.

Operation 3 of the present invention is measuring Raman scattering intensity and uranium luminescence intensity of an unknown sample, calculating a ratio of the measured intensities and determining a concentration thereof by using the calibration curve. Raman scattering intensity of water and uranium luminescence intensity are measured, and the concentration of the unknown sample may be obtained through substituting a value obtained by dividing the measured luminescence intensity by the Raman scattering intensity into the calibration curve of Operation 2.

Hereinafter, the present invention will be described in detail according to examples. However, the following examples are merely presented to exemplify the present invention, and the scope of the present invention is not limited thereto.

EXAMPLE 1

Uranium Concentration Analysis of Unknown Sample

Operation 1: Measuring Raman Scattering Intensity of Water and Uranium Luminescence Intensity Uranium standard solutions in 1 M HClO$_4$ were prepared at concentrations of 0.01 mM, 0.02 mM, 0.05 mM, 0.1 mM, 0.2 mM, 0.5 mM, and 1.0 mM, and each aqueous solution was irradiated with incident light (excitation wavelength) of 310 nm. Raman scattering intensity detected at 346 nm and luminescence intensity detected at 510 nm were then measured by using a fluorophotometer. At this time, a negative voltage applied to a photomultiplier tube (PMT) was 900 V.

Operation 2: Plotting a Calibration Curve

A calibration curve was plotted with the concentration of the uranium standard solution prepared in Operation 1 as x-axis and a value obtained by dividing the luminescence intensity measured for each standard solution by the measured Raman scattering intensity as y-axis.

Operation 3: Determining the Concentration of Unknown Sample

Raman scattering intensity and luminescence intensity were measured in the same manner as Operation 1 except that an unknown sample including uranium was used. It may be understood that the concentration of the unknown sample was 0.074 mM from the calibration curve of Operation 2 through a value of 0.138, which was obtained by dividing the measured luminescence value of 0.46 by the Raman scattering intensity value of 3.34.

EXAMPLE 2

Uranium Concentration Analysis by Using a Semiconductor Laser

Operation 1: Measuring Raman Scattering Intensity of Water and Uranium Luminescence Intensity by Using a Semiconductor Laser Uranium standard solutions in 1 M HClO$_4$ were prepared at concentrations of 5 nM, 20 nM, 50 nM, 100 nM, 200 nM, 500 nM, 1000 nM, 2000 nM, 5000 nM, 0.01 mM, 0.05 mM, 0.1 mM, and 0.2 mM. 1.0 mL of the standard solution was mixed with 1.5 mL of a mixed solution of 0.4 M $H_3PO_4$ and 0.05 M $Na_4P_2O_7$. Each aqueous solution was irradiated semiconductor laser beam of 405 nm in wavelength. Raman scattering intensity detected at 469 nm and luminescence intensity detected at 519 nm were then measured by using a photomultiplier tube coupled with a monochromator. A negative voltage applied to a photomultiplier tube is changed from 500 to 1100 V.

Operation 2: Plotting a Calibration Curve

A Calibration curve for the measurement of uranium concentration was plotted in the same manner as Operation 2 of Example 1.

Operation 3: Determining the Concentration of Unknown Sample

Raman scattering intensity and luminescence intensity were measured in the same manner as Operation 1 of Example 2 except that an unknown sample including uranium was used.

COMPARATIVE EXAMPLE 1

Raman Scattering and Luminescence Measurements of Uranium Aqueous Solution When the Wavelength of Incident Light was 310 nm Raman scattering and luminescence spectra of a uranium aqueous solution were measured by only performing in the same manner as Operation 1 of Example 1 on a 1.0 mM uranium aqueous solution.

COMPARATIVE EXAMPLE 2

Raman Scattering and Luminescence Measurements of Uranium Aqueous Solution When the Wavelength of Incident Light was 355 nm Raman scattering and luminescence spectra of a uranium aqueous solution were measured by only performing in the same manner as Operation 1 of Example 1 except that a 1.0 mM uranium aqueous solution was irradiated with incident light having a wavelength of 355 nm.

COMPARATIVE EXAMPLE 3

Raman Scattering and Luminescence Measurements of Uranium Aqueous Solution When the Wavelength of Incident Light was 414 nm Raman scattering and luminescence spectra of a uranium aqueous solution were measured by only performing in the same manner as Operation 1 of Example 1 except that a 1.0 mM uranium aqueous solution was irradiated with incident light having a wavelength of 414 nm.

COMPARATIVE EXAMPLE 4

Luminescence Intensity Measurement When a Negative Voltage Applied to the Photomultiplier Tube was 600 V Only luminescence intensities were measured on 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 600 V.

COMPARATIVE EXAMPLE 5

Luminescence Intensity Measurement When a Negative Voltage Applied to the Photomultiplier Tube was 700 V Only luminescence intensities were measured on 0.01 mM, 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 700 V.

COMPARATIVE EXAMPLE 6

Luminescence Intensity Measurement When a Negative Voltage Applied to the Photomultiplier Tube was 800 V Only luminescence intensities were measured on 0.01 mM, 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 800 V.

COMPARATIVE EXAMPLE 7

Luminescence Intensity Measurement When a Negative Voltage Applied to the Photomultiplier Tube was 900 V Only luminescence intensity for each concentration was measured on 0.01 mM, 0.02 mM, 0.05 mM, 0.2 mM, 0.5 mM, and 1.0 mM uranium aqueous solutions in the same manner as Operation 1 of Example 1.

COMPARATIVE EXAMPLE 8

Luminescence Intensity Measurement When a Negative Voltage Applied to the Photomultiplier Tube was 1000 V Only luminescence intensities were measured on 0.01 mM, 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 1000 V.

COMPARATIVE EXAMPLE 9

Raman Scattering and Luminescence Intensity Measurements When a Negative Voltage Applied to the Photomultiplier Tube was 600 V Raman scattering and luminescence intensities were measured on 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 600 V.

COMPARATIVE EXAMPLE 10

Raman Scattering and Luminescence Intensity Measurements When a Negative Voltage Applied to the Photomultiplier Tube was 700 V Raman scattering and luminescence intensities were measured on 0.01 mM, 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 700 V.

COMPARATIVE EXAMPLE 11

Raman Scattering and Luminescence Intensity Measurements When a Negative Voltage Applied to the Photomultiplier Tube was 800 V Raman scattering and luminescence intensities were measured on 0.01 mM, 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 800 V.

COMPARATIVE EXAMPLE 12

Raman Scattering and Luminescence Intensity Measurements When a Negative Voltage Applied to the Photomultiplier Tube was 900 V Raman scattering and luminescence intensities were measured on 0.01 mM, 0.02 mM, 0.05 mM, 0.2 mM, 0.5 mM, and 1.0 mM uranium aqueous solutions in the same manner as Operation 1 of Example 1.

COMPARATIVE EXAMPLE 13

Raman Scattering and Luminescence Intensity Measurements When a Negative Voltage Applied to the Photomultiplier Tube was 1000 V Raman scattering and luminescence intensities were measured on 0.01 mM, 0.02 mM, 0.05 mM, 0.2 mM, 0.5 mM, and 1.0 mM uranium aqueous solutions in the same manner as Operation 1 of Example 1 except that a negative voltage applied to the photomultiplier tube was 1000 V.

COMPARATIVE EXAMPLE 14

Raman Scattering and Luminescence Intensity Measurements of Uranium Aqueous Solution by Using a Semiconductor Laser When the Additive Materials were Different Raman scattering and luminescence spectra were measured on 0.1 mM uranium aqueous solution in wavelength range from 450 to 620 nm in the same manner as Operation 1 of Example 2 except that a uranium solution was mixed with three different solutions which were 1 M $HClO_4$, 0.76 M $H_3PO_4$ and a mixed solution of 0.4 M $H_3PO_4$ and 0.05 M $Na_4P_2O_7$ and a negative voltage applied to the photomultiplier tube was 600 V.

COMPARATIVE EXAMPLE 15

Raman Scattering and Luminescence Intensity Measurements by Using a Semiconductor Laser When a Negative Voltage Applied to the Photomultiplier Tube was Changed from 500 to 1100 V Raman scattering and luminescence intensity were measured in the same manner as Operation 1 of Example 2.

EXPERIMENTAL EXAMPLE 1

Movement of Raman Scattering Peak According to the Changes in Incident Light

The following experiments were performed in order to investigate how a Raman scattering peak changes according to the changes in incident light when a sample was water. Wavelengths of incident light to a fluorophotometer used on distilled water were 266 nm, 280 nm, 300 nm, 320 nm, 340 nm, 355 nm, 380 nm, 400 nm, and 414 nm, respectively. Raman scattering intensities with respect to each incident light on the distilled water were measured and Raman scattering peaks therefrom are presented in FIG. 1.

As shown in FIG. 1, it may be understood that the Raman scattering peak of water also moved from a short-wavelength range to a long-wavelength range as the wavelength of the light incident on the sample were changed from a short-wavelength range to a long-wavelength range. Difference between the excitation wavelengths and Raman peaks corresponds to the wavenumber shifts of $3375\pm42$ cm$^{-1}$, which are the overlapped intramolecular Raman bands of water. According to the foregoing results, it may be understood that positions of the Raman scattering peaks may also change according to the changes in the wavelength of the incident light.

EXPERIMENTAL EXAMPLE 2

Absorption and Excitation Spectra of Uranium Aqueous Solution

In order to investigate absorption spectrum and excitation spectrum with respect to a uranium aqueous solution, an absorption spectrum and an excitation spectrum were measured with respect to a uranium aqueous solution prepared at a concentration of 1.0 mM in 1 M $HClO_4$ when a luminescence wavelength was fixed at 510 nm.

Figure 2:
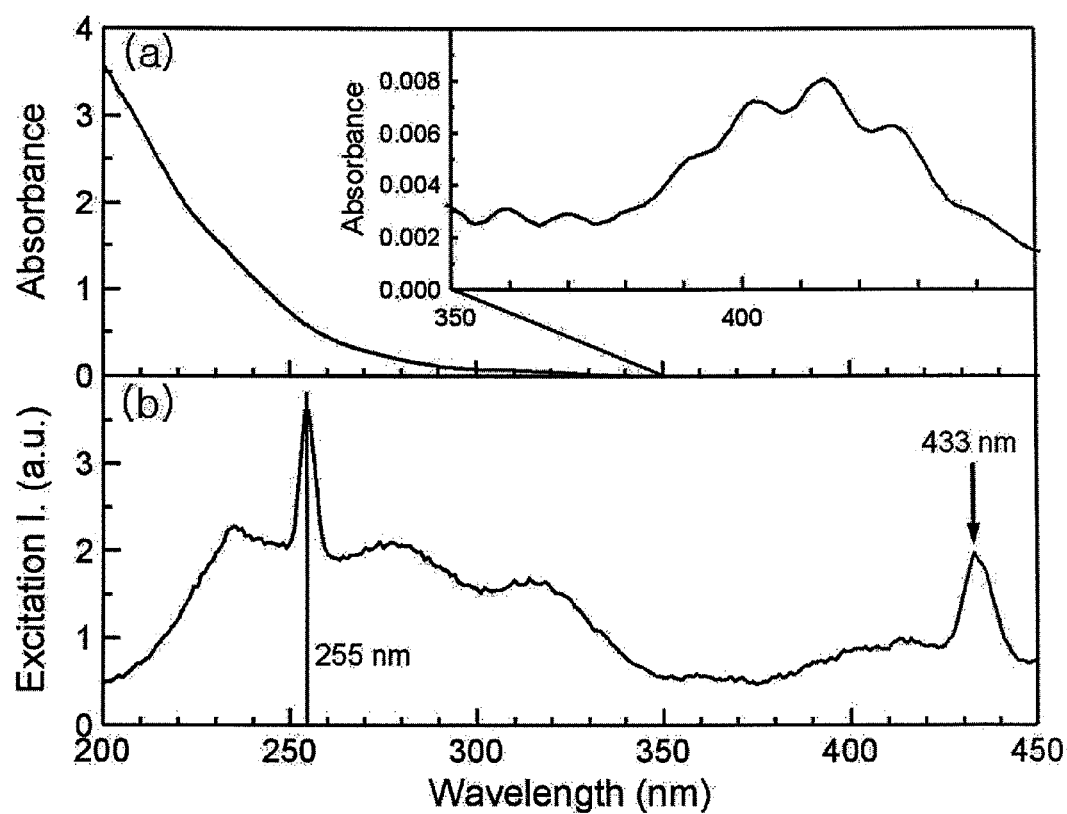
FIGS. 2($a$) is an absorption spectrum of a uranium aqueous solution and 2($b$) is an excitation spectrum when a luminescence wavelength is fixed at 510 nm.

As shown in FIG. 2(a), it may be understood that the absorption spectrum exhibited an inherent absorption spectrum in a visible light range and a maximum absorption wavelength was 414 nm. Also, it may be confirmed that a band structure was absent in a wavelength range of 350 nm or less and absorbance rapidly increased as the wavelength became shorter.

Also, as shown in FIG. 2(b), the excitation spectrum denotes absorption characteristics of uranium (VI) that may generate luminescence at 510 nm in wavelength. A peak appeared at 255 nm resulted from diffraction characteristics of a fluorophotometer when the wavelength of the fluorophotometer for luminescence measurement was fixed at 510 nm, and a peak appeared at 433 nm resulted from a light source generating Raman scattering of water at 510 nm and was unrelated to the absorption characteristics that may cause uranium (VI) luminescence. Since uranium luminescence intensity increased as a wavelength was used in the strong excitation intensity, it may be understood that the uranium luminescence intensity increased when light having a wavelength range of 230 nm to 320 nm was incident as shown in FIG. 2(b) in comparison to when light having a wavelength of 414 nm at which absorption peak maximum are obtained was incident as shown in the inset of FIG. 2(a).

EXPERIMENTAL EXAMPLE 3

Raman Scattering of Water and Uranium Luminescence Spectrum

Figure 3:
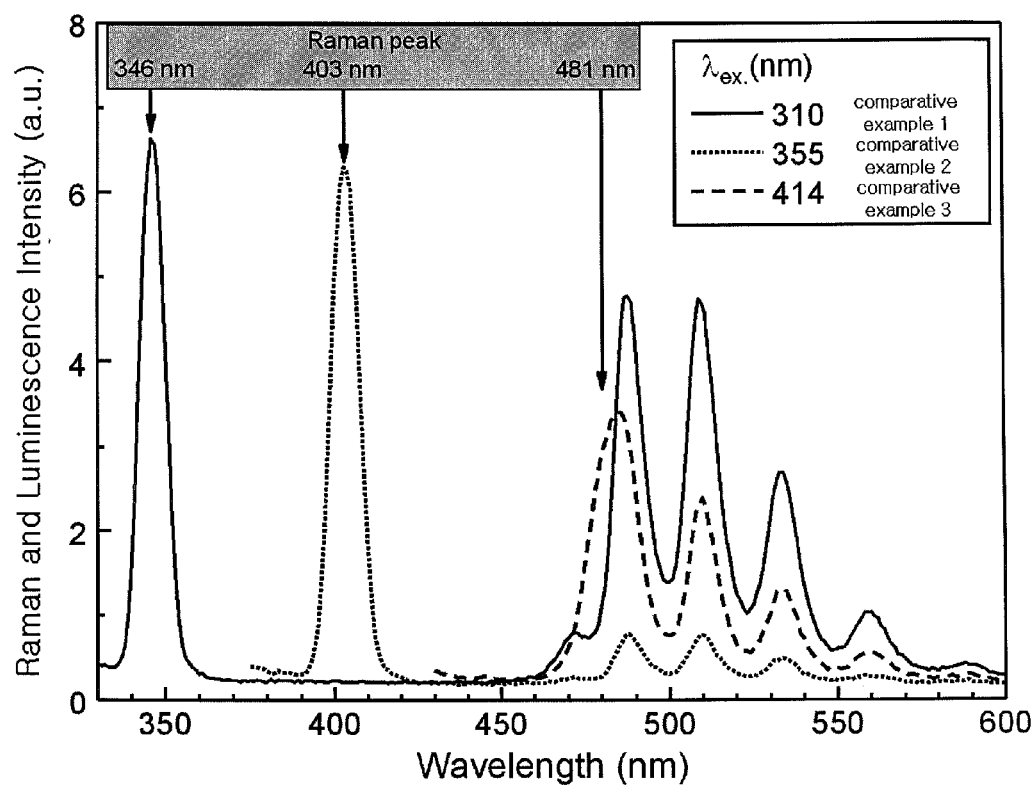
FIG. 3 is a Raman scattering spectrum and a luminescence spectrum of a uranium aqueous solution according to the changes in the wavelength of incident light.

In order to investigate changes in Raman scattering of water and a luminescence spectrum of uranium in an aqueous solution, spectra measured in Comparative Examples 1, 2, and 3 are presented in FIG. 3.

As shown in FIG. 3, Raman scattering peaks of water appeared, in which a center wavelength moved according to the wavelength of incident light, and a typical luminescence spectrum of uranium (VI) was observed within a range of 450 nm to 600 nm. When 355 nm, a third harmonic of a relatively easily usable commercialized Nd:YAG laser, was used (Comparative Example 2), a greatly reduced uranium luminescence intensity was observed together with a Raman scattering peak of water at 403 nm. The reason for this is that excitation intensity at 355 nm was weaker than that at 310 nm, as described in the excitation spectrum shown in FIG. 2. When the light having a maximum absorption wavelength of uranium (VI) of 414 nm was incident (Comparative Example 3), an overlap between the Raman scattering peak of water presented at 481 nm and the uranium luminescence spectrum was observed. Therefore, it may be understood that 414 nm, the maximum absorption wavelength of uranium, was inappropriate to be used as a wavelength of the incident light.

EXPERIMENTAL EXAMPLE 4

Figure 4:
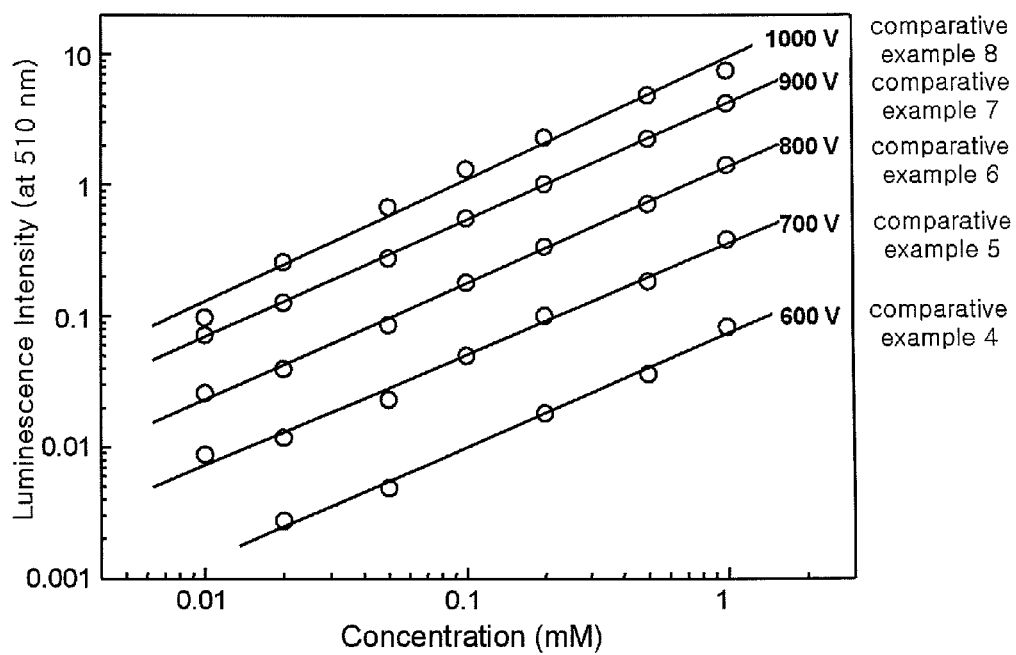
FIG. 4 is a calibration curve illustrating luminescence intensities according to the concentration of uranium aqueous solutions when detector sensitivity is changed.

Luminescence Intensity Measurement According to a Negative Voltage Applied to the Photomultiplier Tube In order to investigate changes in luminescence intensity according to a negative voltage applied to the photomultiplier tube, graphs obtained from Comparative Examples 4 to 8 are presented in FIG. 4.

According to FIG. 4, the wavelength of incident light was fixed at 310 nm and the voltage applied to the photomultiplier tube was changed in five steps (600 to 1000 V). When uranium (VI) luminescence intensity detected at 510 nm was presented as a function of uranium concentration, different calibration curves from one another were obtained. Therefore, the disadvantage of a typical analysis method may be understood, in which a calibration curve must always be repeatedly measured according to the conditions of a detector in order to quantitatively analyzing the uranium of an unknown sample.

EXPERIMENTAL EXAMPLE 5

Figure 5:
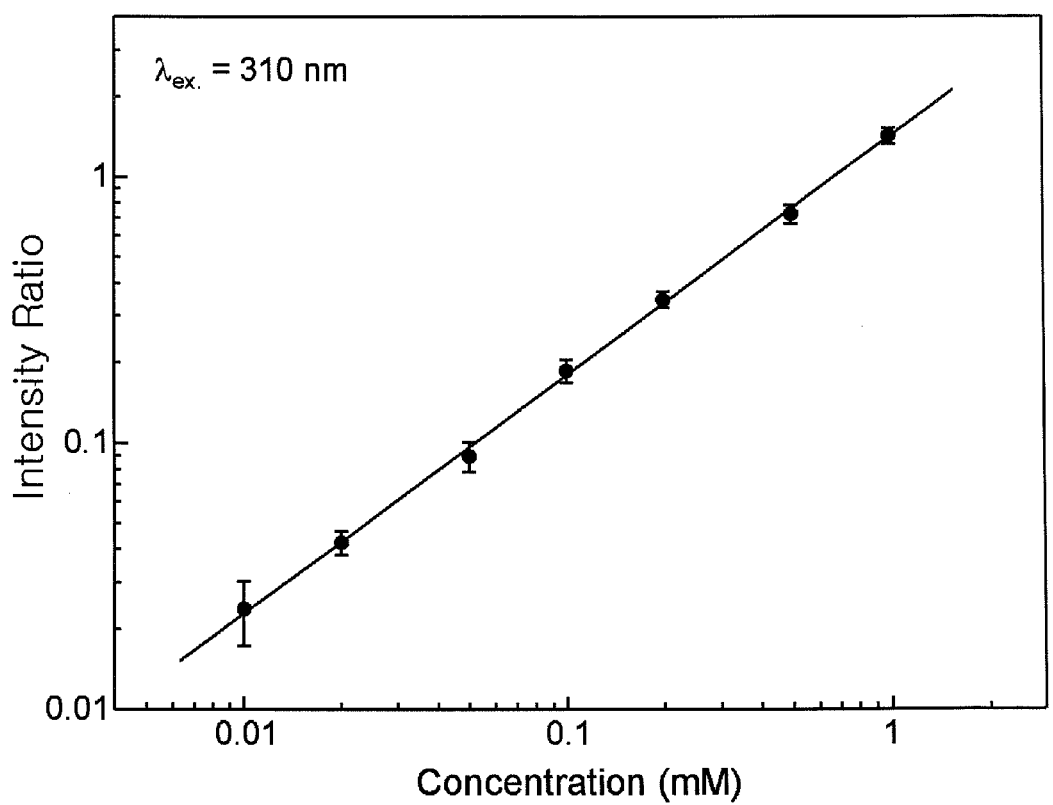
FIG. 5 is a calibration curve illustrating a ratio of luminescence intensity to Raman scattering intensity according to the concentration of uranium aqueous solutions when detector sensitivity is changed.

Measurement of a Ratio of Luminescence Intensity to Raman Scattering Intensity According to a Voltage Applied to the Photomultiplier Tube In order to investigate changes in a ratio of luminescence intensity to Raman scattering intensity for concentrations of uranium standard solutions according to a voltage applied to the photomultiplier tube, a relative value of the luminescence intensity with respect to the Raman scattering intensity measured in respective Comparative Examples 9 to 13 was obtained, and average and standard deviation for each uranium standard solution were then calculated and are presented in FIG. 5.

As shown in FIG. 5, it may be confirmed that the ratio between the luminescence intensity and the Raman scattering intensity according to the uranium concentration was similar to one another despite the negative voltage applied to the photomultiplier tube was changed in five steps (600 to 1000 V). The foregoing results showed average and standard deviation values of five values measured at various voltages applied to the photomultiplier tube. Different from the calibration curve (FIG. 4) changed according to detector sensitivity (voltage applied to the photomultiplier), one of various measurement conditions, it showed that same calibration curve may be obtained when the method of quantitatively analyzing uranium according to the present invention was used. When the method of quantitatively analyzing uranium according to the present invention was used, there were no effects according to the sensitivity of a detector and the intensity of a light source. Therefore, the present invention may remove inconvenience of plotting a calibration curve through standard solutions whenever the quantitative analysis of a uranium solution was performed.

EXPERIMENTAL EXAMPLE 6

Changes in Uranium Luminescence Intensity by Using a Semiconductor Laser According to Additive Solutions In order to investigate changes in luminescence intensity according to additive solutions into uranium standard solutions, spectra obtained from Comparative Example 14 are presented in FIG. 6(a).

In order to enhance the luminescence intensity of uranium in aqueous solutions the standard solution was mixed with luminescence enhancing agents which are 1 M $HClO_4$, 0.76 M $H_3PO_4$ and a mixed solution of 0.4 M $H_3PO_4$ and 0.05 M $Na_4P_2O_7$. As shown in FIG. 6(a), uranium luminescence intensity increases approximately 21 times in 0.76 M $H_3PO_4$ solution and approximately 34 times in a mixed solution of 0.4 M $H_3PO_4$ and 0.05 M $Na_4P_2O_7$ comparing with that in 1 M $HClO_4$ solution.

EXPERIMENTAL EXAMPLE 7

Measurement of a Ratio of Luminescence Intensity to Raman Scattering Intensity by Using a Semiconductor Laser According to a Negative Voltage Applied to the Photomultiplier Tube In order to investigate a calibration curve for the measurement of uranium concentration, a ratio of luminescence intensity to Raman scattering intensity measured in respective Comparative Example 15 was obtained and average and standard deviation for each concentration were then calculated and presented in FIG. 6(b).

Although the peak position of Raman scattering band was close to the position of uranium luminescence peak in wavelength, the Raman scattering intensities at 519 nm were not influenced by the luminescence of uranium at relatively high concentrations. However, the luminescence intensities of uranium at very low concentrations should be corrected with the Raman scattering intensity of pure water. On the other hand the Raman scattering intensity of water at 469 nm should be corrected by the luminescence intensity of uranium at higher concentration than 0.2 mM. The symbols are mean values determined by repeating the experiments over three times and relative standard deviations (RSD) were less than 10%. Linear fit to the ratios of luminescence intensity of uranium to Raman scattering intensity of water resulted in the detection limit of about 5 nM (approximately 1 ppb).

A quantitative analysis method of uranium in an aqueous solution by using a relative ratio between Raman scattering intensity of water and uranium luminescence intensity according to the present invention may greatly reduce inconvenience of a typical analysis method, in which repetitive measurements of calibration curves are required according to various measurement conditions. Also, effective analysis may be conducted because the detection limit thereof is as low as those of inductively coupled plasma atomic emission spectrometry (ICP-AES), inductively coupled plasma mass spectrometry (ICP-MS), and a commercial analysis instrument such as a kinetic phosphorescence analyzer (KPA) by using a laser as a light source. In particular, when a GaN semiconductor laser having a violet wavelength range is used, miniaturization of an analysis apparatus may be possible. Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of quantitatively analyzing uranium in an aqueous solution, the method comprising:

measuring Raman scattering intensity of water and luminescence intensity of uranium for standard solutions having various uranium concentrations by using a fluorophotometer comprising a light source of a continuous wave semiconductor laser;

calculating a ratio of the luminescence intensity of uranium to the Raman scattering intensity of water for each uranium standard solution and plotting a calibration curve therethrough; and measuring Raman scattering intensity of water and luminescence intensity of uranium for an unknown sample by using a fluorophotometer comprising a light source of continuous wave semiconductor laser, calculating a ratio of the luminescence intensity of uranium to the Raman scattering intensity of water and determining a concentration thereof by using the calibration curve, wherein the calculating, plotting and determining steps are performed with a processing device.

2. The method as set forth in claim 1, wherein a light source generating the Raman scattering and the uranium luminescence is a laser beam at an ultraviolet or a blue wavelength.

3. The method of claim 1 wherein the calibration curve is plotted with the uranium concentration of the prepared standard solution as x-axis and a value obtained by dividing the luminescence intensity measured for each concentration by the measured Raman scattering intensity as the y-axis.

4. The method of claim 1 wherein the determining a concentration is performed by reading the value of a concentration on the calibration curve for the calculated ratio.

* * * * *